United States Patent [19]

Kuo et al.

[11] Patent Number: 5,498,715

[45] Date of Patent: Mar. 12, 1996

[54] PROCESS FOR PREPARING IMIDAZOPYRIDINE DERIVATIVES

[75] Inventors: David L. Kuo, Brig; Martin Eyer, Glis; Jean-Paul Roduit, Grone; Alain Wellig, Ried-Morel, all of Switzerland

[73] Assignee: Lonza Ltd., Gamepl/Valais, Switzerland

[21] Appl. No.: 350,083

[22] Filed: Nov. 29, 1994

[30] Foreign Application Priority Data

Dec. 1, 1993 [CH] Switzerland .................... 3580/93

[51] Int. Cl.⁶ .................................................. C07D 471/04
[52] U.S. Cl. .................................................. 546/118
[58] Field of Search ........................................ 546/118

[56] References Cited

U.S. PATENT DOCUMENTS 5,240,938   8/1993   Greenlee et al. ................... 514/303

FOREIGN PATENT DOCUMENTS 0456510   11/1991   European Pat. Off. .

OTHER PUBLICATIONS

Troschütz et al., Arch. Pharm., 325, (1992), pp. 785 to 789.
Horner et al., Ann. 579, pp. 204–211 (1953).
Fieser and Fieser, Advanced Org. Chem., Reinhold Pub., pp. 706–707 (1961).

*Primary Examiner*—Bernard Dentz
*Attorney, Agent, or Firm*—Fisher, Christen & Sabol

[57] ABSTRACT

A process for preparing imidazopyridine derivatives of the general formula:

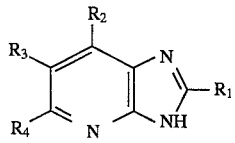

wherein $R_1$ is hydrogen or an alkyl group, and $R_2$, $R_3$ and $R_4$ are identical or different and are hydrogen, an alkyl group, a cycloalkyl group, an aryl group, an aralkyl group or a halogen atom. In this process, a 2-amino-3-nitropyridine is hydrogenated in the presence of a hydrogenation catalyst and the hydrogenation product is condensed with a carboxylic acid simultaneously present in the reaction mixture to give the end product. The imidazopyridine derivatives are intermediates for the preparation of angiotensin II antagonists.

15 Claims, No Drawings

PROCESS FOR PREPARING IMIDAZOPYRIDINE DERIVATIVES

BACKGROUND OF THE INVENTION

1. Field of the Invention

The invention relates to a new process for preparing imidazopyridine derivatives of the general formula:

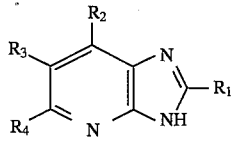

wherein $R_1$ is hydrogen or an alkyl group, and $R_2$, $R_3$ and $R_4$ are identical or different and are hydrogen, an alkyl group, a cycloalkyl group, an aryl group, an aralkyl group or a halogen atom.

2. Background Art

According to European Published Patent Application No. 0456510, 5,7-dimethyl-2-ethylimidazo[4,5b]pyridine is obtained in admixture with 4,6-dimethyl-2,5-bis(propionamido)pyridine by hydrogenation of an isomer mixture of 2-amino-3-nitro-4,6dimethylpyridine and 2-amino-5-nitro-4,6-dimethylpyridine using a palladium catalyst and hydrogen, by subsequent isolation of the resulting mixture of 2,3-diamino and 2,5-diamino isomers and by condensation of this isomer mixture with propionic acid in the presence of polyphosphoric acid. The purification of the desired imidazopyridine is carried out by column chromatography. The isomer mixture of the aminonitropyridines used in the process of European Published patent Application No. 0456510 is obtained by nitration of the corresponding aminopyridine. A considerable disadvantage of this known synthesis is that, over the whole process, an undesired isomer is also reacted which finally results in the end product containing a by-product which is difficult to separate off. The reaction conditions, in particular the long hydrogenation time of 18 hours, likewise make the process unattractive for use on an industrial scale.

BROAD DESCRIPTION OF THE INVENTION

An object of the invention is to provide a process for obtaining the imidazopyridines of the general formula I in a simple manner and on a large scale. Other objects and advantages of the invention are set out herein or are obvious herefrom to one skilled in the art.

The objects and advantages of the invention are achieved by the process of the invention.

The invention involves a process for preparing imidiazopyridine derivatives of the general formula:

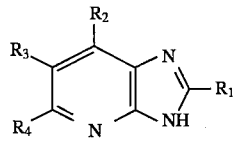

wherein $R_1$ is hydrogen or an alkyl group, and $R_2$, $R_3$ and $R_4$ are identical or different and are hydrogen, an alkyl group, a cycloalkyl group, an aryl group, an aralkyl group or a halogen atom. In the process a 2-amino-3-nitropyridine of the general formula:

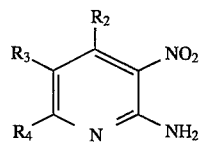

wherein $R_2$, $R_3$ and $R_4$ are as defined above, is hydrogenated with hydrogen in the presence of a carboxylic acid of the general formula:

$$R_1COOH \qquad III$$

wherein $R_1$ is as defined above and a hydrogenation catalyst, with the hydrogenation product formed being condensed with the carboxylic acid of the general formula III to give the end product.

Preferably the reaction is carried out in the additional presence of a catalytic amount of an acid. Preferably sulfuric acid is used in a catalytic amount of from 1 to 20 percent by weight, based on the 2-amino-3-nitropyridine of the general formula II. Preferably the hydrogenation catalyst used is a palladium catalyst. Preferably the reaction is carried out at a $H_2$ pressure of from 1 bar to 30 bar and a temperature between 100° and 150° C. Preferably the carboxylic acid used is propionic acid. Preferably the 2-amino-3-nitropyridine of the general formula II used is 2-amino-4,6-dimethyl-3-nitropyridine.

The imidazopyridine derivatives of the general formula I are used for the preparation of angiotension II antagonists (European Published Patent Application No. 0456510).

DETAILED DESCRIPTION OF THE INVENTION

The terms used for the individual radicals $R_1$ to $R_4$ in the formulae herein have the following meaning.

The term alkyl group means a straight-chain or branched alkyl group having advantageously from 1 to 6 carbon atoms, preferably having from 1 to 4 carbon atoms. Examples of such preferred alkyls are methyl, ethyl, n-propyl, i-propyl, n-butyl and t-butyl. The term cycloalkyl group advantageous means a $C_3$–C6-cycloalkyl group, such as, a cyclopropyl, a cyclobutyl, a cyclopentyl or a cyclohexyl group. The term aryl includes carbocyclic aromatics, advantageous phenyl or naphthyl. The term aralkyl denotes an aryl-substituted alkyl group, advantageously a phenyl-substituted ($C_1$–$C_6$)-alkyl group, in particular benzyl.

Halogen is fluorine, chlorine, bromine or iodine; the preferred halogen is chlorine.

The specific groups, in particular the cyclic radicals, can in each case be monosubstituted or polysubstituted. Suitable substituents radicals are, for example, halo, nitro, amino, alkylamino, dialkylamino, hydroxy, alkoxy, alkyl or alkanoyl.

The 2-amino-3-nitropyridine of the general formula:

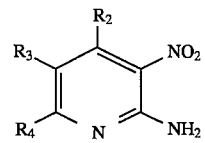

wherein $R_2$, $R_3$ nd $R_4$ are as defined above, is preferably obtained by reaction of 1,1-diamino-2-nitroethene of the formula:

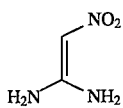

with a 1,3-dicarbonyl compound of the general formula:

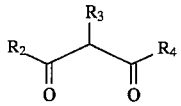

wherein $R_2$, $R_3$ and $R_4$ are as defined above.

For the example of the reaction of 1,1-diamino-2-nitroethene with acetylacetone to give 2-amino-3-nitro-4,6-dimethylpyridine, this reaction is described by Troschütz et al., in Arch. Pharm., 325 (1992), 785–789. A yield of 52 percent is described.

By selection of a suitable solvent, the yield can be increased to over 90 percent. Thus, the reaction is preferably carried out at reflux temperature in 2-methoxyethanol. The corresponding 2-amino-3-nitropyridine is obtained in this process as a pure isomer and can be used in the reaction of the invention without additional purification.

According to the invention, the 2-amino-3-nitropyridine of the general formula II is hydrogenated with hydrogen in the presence of a carboxylic acid of the general formula:

$R_1COOH$  III wherein $R_1$ is as defined above, and a hydrogenation catalyst, with the hydrogenation product formed being condensed with the carboxylic acid of the general formula III to give the end product. Preference is given to starting from 2-amino-3-nitro- 4,6-dimethylpyridine.

The reaction is advantageously carried out in the presence of a catalytic amount of an additional acid. This gives a more rapid reaction and an increased yield.

Suitable additional acids are, for example, sulfuric acid, phosphoric acid or p-toluenesulphonic acid. Preference is given to using sulfuric acid in an amount of from 1 to 20 percent by weight, particularly preferably in an amount of about 5 percent by weight, based on the aminonitropyridine used.

Suitable hydrogenation catalysts are platinum oxide or palladium on an inert support. Preference is given to using from 2 to 10 percent by weight of palladium, applied to carbon in an amount of from 5 to 10 percent.

The carboxylic acid of the general formula III which is used is advantageously formic acid, acetic acid, propinonic acid or butyric acid, preferably propionic acid. In general, the carboxylic acid of the general formula III simultaneously acts as a solvent. However, an inert solvent, such as, a lower aliphatic alcohol or a lower aliphatic nitrile, can be added.

The reaction is advantageously carried out at a $H_2$ pressure of from 1 bar to 30 bar and a reaction temperature of 100° to 150° C. After a reaction time of generally from about 2 hours to 10 hours, and conventional work-up, which comprises separating off the catalsyt, recycling excess carboxylic acid and extraction with a suitable solvent, the desired imidazopyridine derivative can be obtained in good yield and quality.

EXAMPLE 1

Preparation of 2-amino-3-nitro-4,6-dimethylpyridine 3 g (29.1 mmol) of 1,1-diamino-2-nitroethene and 11.6 (17.4 mmol) of acetylacetone were maintained at reflux in 40 ml of 2methoxyethanol for 6 hours. The solvent was then removed in vacuo, the residue was slurried in 20 ml of iced water and filtered. Drying of the filter cake gave 4.52 (93 percent) of the title product. The product had a melting point of 165° C. Other data concerning the product was:
$^1$H NMR (CDCl$_3$, 400 MHz) δ in ppm
  2.37 (s, 3H);
  2.54 ( s, 3H);
  6.38 (bs, 2H);
  6.44 (s, 1H).

EXAMPLE 2

Preparation of 5,7-dimethyl-2-ethylimidazo[4,5b]pyridine 4 g (23.9 mmol) of 2-amino-3-nitro-4,6-dimethylpyridine, 0.2 g (5 percent by weight) of 10 percent Pd/C and 50 ml of propionic acid were charged into an autoclave. This was then pressurized with 20 bar of $H_2$ and hydrogenation was carried out for 7.5 hours at 130° C. The autoclave was then vented and 15 ml of propionic acid/water was azeotropically distilled off. The autoclave was then again pressurized with 20 bar of $H_2$ and the reaction was carried out for a further 5 hours at 130° C. After cooling to 20° C., the autoclave was vented and the catalyst was filtered off. The filtrate was evaporated, the residue was admixed with 25 ml of water and adjusted to pH 9 using sodium hydroxide solution. After extraction of the aqueous phase with methylene chloride, the title product could be obtained from the organic extract in a crude yield of 4.17 g (84.3 percent), GC purity 84.8 percent. Crystallization in acetone gave a pure product in the form of pale yellow crystals. The melting point of the product was 148° to 150° C. Other data concerning the product was:
$^1$H NMR (DMSO-d$_6$, 400 MHz) δ in ppm
  1.32 (t, 3H);
  2.46 (s, 6H);
  2.83 (q, 2H);
  6.84 (s, 1H);
  12.44 (bs, 1H).

EXAMPLE 3

The procedure was similar to that in Example 2. In addition, 0.2 g (5 percent by weight) of sulfuric acid was initially charged. After hydrogenation (7.5 hours, 20 bar, 130° C.), the catalyst was filtered off and the reaction mixture was stirred for 3.5 hours at 140° C. The resulting water was azeotropically distilled off. After work-up as described in Example 2, the title product was obtained in a crude yield of 4.21 g (90 percent), GC purity 89.6 percent. Crystallization from acetone gave a pure product having a purity of 97.5 percent. The product had a melting point of 148° to 150° C.

What is claimed is:

1. A process for preparing a imidazopyridine derivative of the formula:

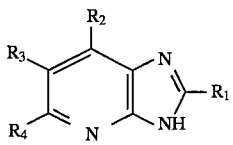

wherein $R_1$ is hydrogen or an alkyl group, and $R_2$, $R_3$ and $R_4$ are identical or different and are hydrogen, an alkyl group, a cycloalkyl group, an aryl group, an aralkyl group or a halogen atom, comprising hydrogenating a 2-amino-3-nitropyridine of the formula:

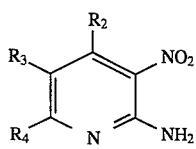

wherein $R_2$, $R_3$ and $R_4$ are as defined above, with hydrogen in the presence of (i) a carboxylic acid of the formula:

$$R_1COOH \qquad \text{III}$$

wherein $R_1$ is as defined above, (ii) a hydrogenation catalyst, and (iii) a catalytic amount of acid other than the carboxylic acid of the formula III, with the hydrogenation product formed being condensed with the carboxylic acid of the formula III to give the imidapopyridine derivative of the formula I.

2. The process according to claim 1 wherein sulfuric acid is used in a catalytic amount of from 1 to 20 percent by weight, based on the 2-amino-3-nitropyridine of the formula II.

3. The process according to claim 2 wherein the hydrogenation catalyst used is a palladium catalyst.

4. The process according to claim 3 wherein the reaction is carried out at a $H_2$ pressure of from 1 bar to 30 bars and a temperature between 100° and 150° C.

5. The process according to claim 4 wherein the carboxylic acid used is propionic acid.

6. The process according to claim 5 wherein the 2-amino-3-nitropyridine of formula II used is 2-amino-4,6-dimethyl-3-nitropyridine.

7. The process according to claim 1 wherein the hydrogenation catalyst is a palladium catalyst.

8. The process according to claim 1 wherein the reaction is carried out at a $H_2$ pressure of from 1 bar to 30 bars and a temperature between 100° and 150° C.

9. The process according to claim 1 wherein the 2-amino-3-nitropyridine of the formula II used is 2-amino-4,6-dimethyl- 3-nitropyridine.

10. The process according to claim 1 wherein the carboxylic acid used is propionic acid.

11. The process according to claim 1 wherein $R_1$ in formula III is an alkyl group.

12. The process according to claim 1 wherein the additional acid is selected from the group consisting of sulfuric acid, phosphoric acid and p-toluenesulfonic acid.

13. The process according to claim 1 wherein the carboxylic acid of the formula III is selected from the group consisting of formic acid, acetic acid, propionic acid and butyric acid.

14. The process according to claim 1 wherein an inert solvent is also present.

15. The process according to claim 1 wherein the hydrogenation catalyst is platinum oxide or platinum on an inert support.

* * * * *